United States Patent [19]

Kondo et al.

[11] Patent Number: 4,981,137
[45] Date of Patent: Jan. 1, 1991

[54] MAGNETIC RESONANCE IMAGING APPARATUS

[75] Inventors: Syouzi Kondo; Michihiko Aoki, both of Katsuta, Japan

[73] Assignee: Hitachi, Ltd., Tokyo, Japan

[21] Appl. No.: 343,809

[22] Filed: Apr. 27, 1989

[30] Foreign Application Priority Data

Apr. 28, 1988 [JP] Japan .................................. 63-106196

[51] Int. Cl.⁵ ............................................ A61B 5/055
[52] U.S. Cl. .................................. 128/653 A; 324/318; 381/94; 381/168
[58] Field of Search ...................... 128/653; 381/92, 94, 381/25, 26, 28, 67; 379/167; 324/309, 307, 318

[56] References Cited

U.S. PATENT DOCUMENTS

| | | |
|---|---|---|
| 4,410,770 | 10/1983 | Hagey ..................................... 381/92 |
| 4,689,565 | 8/1987 | Kemner et al. ....................... 324/318 |
| 4,696,030 | 9/1987 | Egozi ..................................... 381/94 |
| 4,701,952 | 10/1987 | Taylor ..................................... 381/67 |
| 4,903,703 | 2/1990 | Igarashi et al. .................. 128/653 A |

Primary Examiner—Kyle L. Howell
Assistant Examiner—K. M. Pfaffle
Attorney, Agent, or Firm—Antonelli, Terry, Stout & Kraus

[57] ABSTRACT

A magnetic resonance imaging apparatus for taking a pateint into a air-core of a static magnetic field coil which forms a static magnetic field and a gradient coil which forms a gradient magnetic field and imaging a tomogram of the patient comprising, a microphone disposed in a domain which is on the extension of an air-core and out of the end of the static magnetic field coil, wherein a directivity axis of the microphone is directed to the patient, an amplifier for amplifying an output signal of the microphone, and a first loudspeaker which is connected to the amplifier.

Operator clearly hear the patient's voice in spite of the noise of the striking sound generated from the gradient coil.

10 Claims, 1 Drawing Sheet

MAGNETIC RESONANCE IMAGING APPARATUS

BACKGROUND OF THE INVENTION

The present invention relates to a magnetic resonance imaging apparatus wherein a patient is disposed within an air-core of a static magnetic field generating means which forms a static magnetic field a gradient coil forms a gradient magnetic field within the air-core and a tomogram of the patient is imaged, and more particularly relates to the magnetic resonance imaging apparatus having a voice communication apparatus which is suitable for transmitting an operator's voice to the patient directly.

The conventional magnetic resonance imaging apparatus is constructed with a magnetic shielding room around the static magnetic field generating means which prevents the static magnetic field from being effected by electrically conductive materials at the outside of the magnetic shielding room so as to keep a homogeneity of the static magnetic field, and an electric wave shielding room around the magnetic shielding room for stably receiving an imaging signal generated by magnetic resonance phenomenon without receiving any affection of external noise.

In imaging the tomogram of the patient using the magnetic resonance imaging apparatus, it is necessary for the operator to communicate with the patient using a voice communication apparatus in order to correctly and speed by understand the state or the condition of the patient.

In the general magnetic resonance imaging apparatus, the most popular one is an apparatus having a voice tube using an electrically non-conductive material, wherein one side of the voice tube is close to the mouth of the patient and the other side is close to a microphone which transmits the patient's voice to the operator who is outside of the shielding room. On the other side, the operator's voice is transmitted to the patient by a loudspeaker which is installed on a wall or a ceiling in the shielding room.

The Japanese Patent Laid-open No. 60-207653 and the Japanese Utility Model Laid-open No. 61-16105 are cited as examples of such device.

But the conventional technique as stated above has the following drawbacks.

(1) As the voice tube is set close to the mouth of the patient, the patient could not help feeling a sense of oppression of the voice tube. It is troublesome for the patient.

(2) In imaging the tomogram of the patient, a striking sound is generated from the gradient coil and is transmitted with the patient's voice to the operator through the voice tube. It is difficult for the operator to distinguish the patient's voice from the striking sound. Furthermore, as the patient always moves in order to change the position of the patient's body which is being imaged, it is very difficult to set the voice tube at a position so as to be able to reduce the striking sound and thereby enable distinguishing of the patient's voice from the striking sound.

SUMMARY OF THE INVENTION

The present invention is directed to overcoming the above mentioned problem of the conventional technique.

An object of present invention is to provide a magnetic resonance imaging apparatus having a voice communication apparatus which is suitable for the clear and reliable communication of the operator with the patient in spite of the striking sound generated from the gradient coil.

In order to attain the above object, a magnetic resonance imaging apparatus of the present invention is provided with a unidirectional microphone disposed in a domain which is on the extension of an air-core and beyond an end of the static magnetic field generating means or a gradient coil, wherein a directivity axis of the unidirectional microphone is directed to the patient.

Furthermore, in the, magnetic resonance imaging apparatus stated above, there is provided a filter so as to select the frequencies of the voice signal transmitted from the unidirectional microphone different from that of the striking sound.

DETAILED DESCRIPTION OF THE PREFERRED EMBODIMENTS

Figure 1:
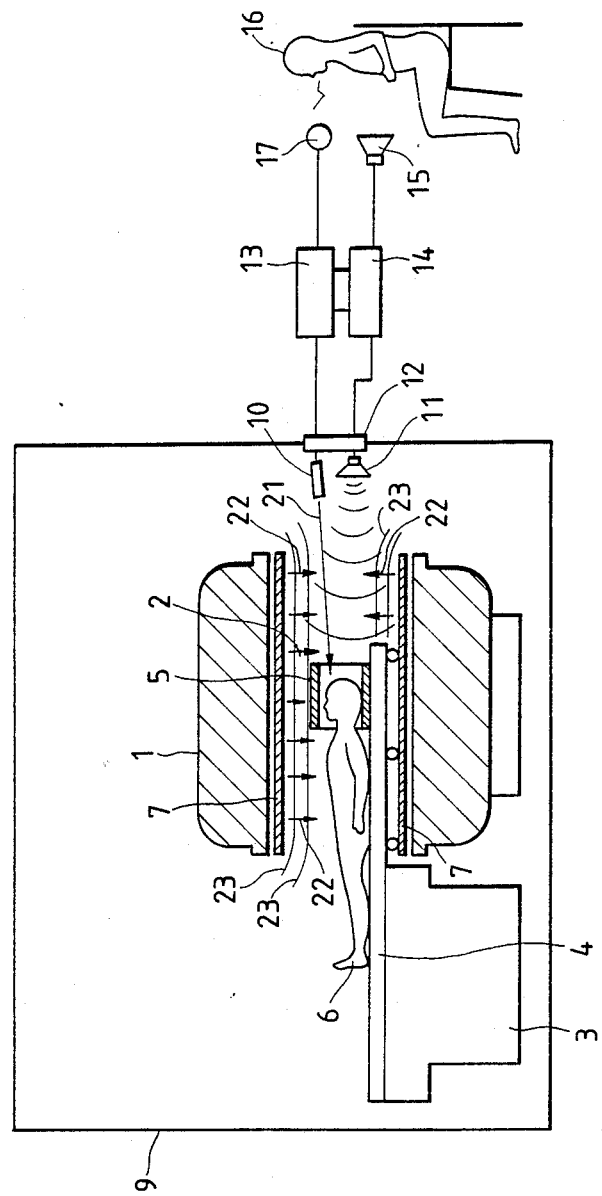
FIG. 1 is a schematic view showing an embodiment of a magnetic resonance imaging apparatus in the present invention.

FIG. 1 shows an embodiment of a magnetic resonance imaging apparatus in the present invention having a super conductive magnet 1 which forms a static magnetic field and a gradient coil 7 which forms a gradient magnetic field in an air-core 2 of the superconductive magnet 1.

The super conductive magnet 1 is set in an electric wave shielding room 9 and forms the static magnetic field which is directed to the central axis of the magnet 1 in the air-core 2. A board 4 is slidably provided on a bed 3 and a coil 5 is installed on one side of the board 4. The patient 6 is laid on the board 4 so as to hold the body portion within the coil 5. FIG. 1 shows the case that the body portion in the coil 5 is a head, for example.

By slidably moving the board 4 on which the patient is laid, the portion of the patient which should be imaged is guided into the air-core 2 of the super conductive magnet 1, and the coil 5 emits a high frequency electric wave so as to receive a magnetic resonance imaging signal from which the tomogram is obtained. At the inner surface of the superconductive magnet 1, the gradient coil 7 is disposed in order to generate the gradient field in the air-core 2. A unidirectional microphone 10 which detects a voice of the patient is disposed at a position on the extension of the air-core 2 of the magnet 1 and outside of the end of the superconductive magnet 1 at a position where the static magnetic field is not formed. And further at the same time, the microphone 10 is disposed at the outside of the end of the gradient coil 7, and a directivity axis 21 of the microphone 10 is directed to the portion of the patient near the mouth of the patient and far from the gradient coil 7. It is best to direct the directivity axis 21 of the microphone to the mouth of the patient and at least the axis 21 should be directed to the air-core 2 and should not be directed to the gradient coil 7 directly. If the directive characteristics of the microphone 10 is not so high, the microphone 10 picks up a pretty big striking sound with the voice sound of the patient, and on the contrary, if it is so high, the loudness of the voice sound from the microphone is highly changed according to the moving of the mouth position. Therefore, the directive characteristics of the microphone should be selected so as to be able to always pick up the voice sound of the patient who moves to different positions and not to pick up a loud striking sound. Further, as long as the directivity axis 21 of the microphone is not directed to the gradient coil directly, it can be moved so as to direct to the mouth of the patient by changing the position of the microphone 10.

In FIG. 1, numeral 22 denotes a transmitting direction of the striking sound generated from the gradient coil 7. And as the transmitting direction 22 is nearly perpendicular to the directivity axis of the microphone 10 and the microphone 10 is disposed outside of the end of the gradient coil 7, the striking sound transmitted to the microphone is very small and the voice of the patient is clearly detected by the microphone 10, and since at the same time, as the microphone 10 is out of the static magnetic field, the homogeneity of the static magnetic field is not disturbed by the microphone 10. Furthermore, as the patient is laid so as to extend substantially along the directivity axis of the microphone 10, the voice sound is clearly picked up by the microphone 10 is spite of moving of the patient to the direction of the central axis of the superconductive magnet 1 in the air-core 2. Numeral 23 shows an isobaric sound pressure line of the striking sound.

Numeral 11 denotes a loudspeaker which is disposed at the position which is on the extension of the air-core 2 of the superconductive magnet 1 so as not to disturb the homogeneity of the static magnetic field.

The unidirectional microphone 10 is connected to a filter 12 which is mounted on a wall of the electric wave shielding room 9. The filter 12 is connected to a frequency equalizer 13 connected to an amplifier 14. The voice signal from the patient detected by the microphone 10 is mixed a little with the striking sound signals generated from the gradient coil 7. The filter 12 selects the frequencies of the voice signal which different from those of the striking sound. Furthermore, the frequency equalizer 13 amplifies the frequencies of the voice signal from the filter which are different from those of the striking sound and reduces the frequencies of the striking sound slightly mixed with the voice sound. The amplifies 14 amplifies the voice sound from the frequency equalizer and a loudspeaker 15 converts the voice signal from the equalizer 13 into a voice sound. We experimentally confirmed that the frequencies of the striking sound are from 250 to 650 Hz. The frequencies of the voice sound are from 150 to 3000 Hz. Then, the filter 12 selects the frequencies from 650 to 3000 Hz so as to pass the voice signal only and cut off the frequencies below 650 Hz so as to not pass a striking sound signal, and the equalizer 13 amplifies the frequencies from 650 to 3000 Hz of the voice signal and reduces the frequencies below 650 Hz of the striking sound signal. Therefore, the operator 16 can hear the patient's voice clearly.

On the other hand, the operator's voice is transmitted to the patient through a microphone 17, the equalizer 13, the amplifier 14, the filter 12 and the loudspeaker 11. When transmitting the operator's voice to the patient, the frequencies of the background noise in an operator's room is almost from 0 to 650 Hz. So, the filter 12 and the equalizer 13 are useful for suppressing the background noise, and make it possible to clearly transmit the operator's voice to the patient.

Further, as the loudspeaker is disposed on the extension of the air-core 2 of the superconductive magnet 1 and outside of the end thereof, for example, at a sidewall of the electric wave shielding room, the static magnetic field is not disturbed by the loudspeaker 11.

In some case, only the transmitting means for sending the operator's voice to the patient is useful, and the transmitting means for sending the patient's voice to the operator is not needed.

We claim:

1. A magnetic resonance imaging apparatus for imaging a tomograph of a patient comprising,
   a static magnet for forming a static magnetic field in an air-core of the static magnet and into which the patient is disposed,
   a gradient coil for forming a gradient magnetic field in the air-core,
   a microphone disposed at a position along an extension of the air-core outside of an end portion of the static magnet and having a directivity axis directed to the patient and extending so as to be substantially perpendicular to a transmitting direction of a striking sound generated from a surface of the gradient coil,
   coupled to the microphone for amplifying an output signal from the microphone, and
   a first loudspeaker means connected to the amplifier for converting the amplified signal from the amplifier into sound.

2. A magnetic resonance imaging apparatus defined in claim 1, further comprising,
   filter means coupled to the microphone and the amplifier for selecting frequencies of the output signal from the microphone and for supplying the output signal having the selected frequencies to the amplifier.

3. A magnetic resonance imaging apparatus defined in claim 1, further comprising:
   an electric wave shielding room for accommodating the static magnet, the gradient coil, and the microphone; the amplifier and the first loudspeaker being disposed outside of the electric wave shielding room.

4. A magnetic resonance imaging apparatus defined in claim 1, further comprising,
   a second loudspeaker means disposed along the extension of the air-core for transmitting an operator's voice to the patient.

5. A magnetic resonance imaging apparatus defined in claim 1, wherein said microphone is a unidirectional microphone.

6. A magnetic resonance imaging apparatus for imaging a tomograph of a patient comprising,
   a static magnet for forming a static magnetic field in an air-core of the static magnet and into which the patient is disposed,
   a gradient coil for forming a gradient magnetic field in the air-core,
   a microphone disposed at a position along an extension of the air-core outside of an end portion of the gradient coil and having a directivity axis directed to the patient and extending so as to be substantially perpendicular to a transmitting direction of a striking sound generated from a surface of the gradient coil,
   amplifier means coupled to the microphone for amplifying an output signal from the microphone, and
   a first loudspeaker means connected to the amplifier for converting the amplified signal from the amplifier into sound.

7. A magnetic resonance imaging apparatus defined in claim 5, further comprising,
   filter means for selecting frequencies of the output signal from the microphone and supplying the output signal having the selected frequencies to the amplifier.

8. A magnetic resonance imaging apparatus defined in claim 5, further comprising,
   a magnetic shielding room for accommodating the static magnet, the gradient coil, and the microphone; the amplifier and the first loudspeaker being disposed outside of the magnetic shielding room.

9. A magnetic resonance imaging apparatus defined in claim 5, further comprising:
   a second loudspeaker means disposed along the extension of the air-core for transmitting an operator's voice to the patient.

10. A magnetic resonance imaging apparatus defined in claim 6, wherein
    said microphone is a unidirectional microphone.

* * * * *